United States Patent [19]

Cartmell et al.

[11] Patent Number: 5,160,328
[45] Date of Patent: Nov. 3, 1992

[54] HYDROGEL BANDAGE

[75] Inventors: James V. Cartmell, Xenia; Wayne R. Sturtevant, Centerville, both of Ohio

[73] Assignee: NDM Acquisition Corp., Minneapolis, Minn.

[21] Appl. No.: 741,317

[22] Filed: Aug. 7, 1991

[51] Int. Cl.⁵ .................. A61F 13/02; A61L 15/00; C08L 15/00
[52] U.S. Cl. .................. 604/307; 604/304; 523/111; 602/41; 602/43; 602/44; 602/47; 602/59
[58] Field of Search .......... 128/155, 156, 888; 604/304, 307; 523/111; 602/41–45, 47, 48, 52, 54, 57–59

[56] References Cited

U.S. PATENT DOCUMENTS

| | | |
|---|---|---|
| 4,226,232 | 10/1980 | Spence . |
| 4,377,160 | 3/1983 | Romaine . |
| 4,393,048 | 7/1983 | Mason, Jr. et al. . |
| 4,496,535 | 1/1985 | Gould et al. .......... 523/111 |
| 4,657,006 | 4/1987 | Rawlings et al. . |
| 4,770,299 | 9/1988 | Parker . |
| 4,807,613 | 2/1989 | Koehnke et al. .......... 128/155 |
| 4,867,821 | 9/1989 | Morgan . |
| 4,899,738 | 2/1990 | Parker . |
| 4,901,714 | 2/1990 | Jensen .......... 128/155 |
| 4,909,244 | 3/1990 | Quarfoot et al. .......... 128/155 |
| 4,911,155 | 3/1990 | Delannoy . |
| 5,003,970 | 4/1991 | Parker et al. . |
| 5,006,401 | 4/1991 | Frank . |
| 5,025,783 | 6/1991 | Lamb . |

FOREIGN PATENT DOCUMENTS

| | | |
|---|---|---|
| 48769/90 | 1/1990 | Australia . |
| 2367/80 | 11/1980 | Ireland . |
| 90/03155 | 4/1990 | World Int. Prop. O. .......... 128/156 |

*Primary Examiner*—David Isabella
*Assistant Examiner*—Anthony P. Zuttarelli
*Attorney, Agent, or Firm*—Killworth, Gottman, Hagan & Schaeff

[57] ABSTRACT

A self-adhesive bandage is provided. The bandage comprises a substrate having a first side and a second side and a plurality of layers including a backing layer which forms the first side of the substrate, and an adhesive layer which forms the second side of the substrate. A hydrogel layer is disposed over the second side of the substrate and is made from a polyurethane hydrogel material especially suitable for absorbing bodily fluids, such as wound exudate. Additionally, a plurality of support layers may be interposed between the substrate and the hydrogel layer to provide the bandage with additional support.

19 Claims, 1 Drawing Sheet

1

HYDROGEL BANDAGE

BACKGROUND OF THE INVENTION

The present invention relates to an improved bandage, and more particularly, to a bandage containing a polyurethane hydrogel material suitable for absorbing bodily fluids such as wound exudate without adhering to a wound on which the bandage is mounted.

In the art of protecting minor cuts, scratches, abrasions, and similar injuries, particularly on a temporary, self-treatment basis, the use of the so-called self-adhesive bandage has become widespread. Bandages, such as the self-adhesive type, essentially involve a length of adhesive tape with a pad of gauze, or similar material, located in the center portion thereof, the entire length being covered by a separable layer of release paper or liner which preserves the sterility of the gauze, and renders the adhesive properties of the paper inoperative until the paper is removed prior to application of the bandage. Such bandages are commercially available in a variety of shapes and sizes and are both inexpensive and easy to apply, which helps to account for their widespread popularity.

One problem, however, with these bandages is that the gauze portion of the bandage has a tendency to become saturated with wound exudate. As the wound exudate dries, it forms an adherent bond between the bandage and the wound. Accordingly, when an attempt is made to remove the bandage from the wound, the result is not only painful, but in addition, the new cell tissue forming is torn away from the wound, thereby inhibiting the healing process. A further consequence of having a bandage with a gauze pad saturated with wound exudate is that the wound is extremely vulnerable to infection. In an attempt to avoid this problem, the gauze portion of the bandage has been treated with or formed from hydrophobic fibers such as synthetic fibers. Such attempts, however, have not avoided the adherency which has been experienced between the wound and the gauze due, in part, to the tendency of wound and other bodily fluids penetrating around the fibers and into the interior of the gauze. The bodily fluids, including wound exudate, perspiration, etc., tend to solidify, thereby creating the undesired adherence between the bandage and the wound. There have also been attempts to incorporate sheets of hydrophobic materials, as opposed to gauze, adjacent to the wound surface. The surface irregularities of these sheets, however, facilitate formation of the bond between the bandage and the wound and therefore, do not provide a viable alternative.

In yet another attempt to provide an improved bandage of the self-adhesive type, Morgan, U.S. Pat. No. 4,930,500, discloses a self-adhesive bandage which comprises a hydrophilic gel located on a bandage carrier strip. The hydrophilic gel comprises water and a polyol mixed with the reaction product of a bis-crosslinking agent with an acrylamide compound. While such a hydrophilic gel may avoid or minimize the adherence of the bandage with the wound over which it is placed, it does not absorb sufficient quantities of wound exudate and/or other bodily fluids to promote the healing of the wound satisfactorily. Furthermore, the hydrophilic gel material, as disclosed by Morgan, has a tendency to break apart upon absorption of such fluids. Thus, upon removal of the bandage from the wound, the hydrophilic gel material breaks apart leaving fragments and pieces of gel material in the wound such that the healing process of the wound is inhibited. Moreover, the bandage disclosed in Morgan is not made from transparent materials and thus, the wound may not be visually inspected without removing the bandage. As is known, frequent removal and replacement of the bandage tends to inhibit the healing process since new cell tissue is destroyed upon each removal.

Accordingly, there is a need for a bandage of the self-adhesive type which includes a material having the ability to absorb sufficient amounts of wound exudate and other body fluids and satisfactorily promote the healing of the wound yet maintain its structural integrity even upon removal of the bandage from the wound. There is also a need for a bandage which permits visual inspection of the wound without removing the bandage from the wound.

SUMMARY OF THE INVENTION

The present invention meets the aforementioned needs by providing a bandage of the self-adhesive type which includes a material having the ability to absorb sufficient amounts of wound exudate and other body fluids and satisfactorily promote the healing of the wound yet maintain its structural integrity even upon removal of the bandage from the wound. The present invention also provides a bandage which permits visual inspection of the wound without removing the bandage from the wound. Thus, the bandage of the present invention promotes the healing of wounds on which it is mounted.

In accordance with one aspect of the invention, the bandage comprises a backing layer, a pressure sensitive adhesive layer coated onto a side of the backing layer for contacting the skin of a patient, and a hydrogel layer formed on the adhesive layer. The hydrogel layer is formed of a polyurethane hydrogel material suitable for absorbing bodily fluids. The side of the backing layer which contacts the patient's skin comprises a first portion being formed of the adhesive layer and a second portion being formed of the hydrogel layer. The bandage may include a support layer to provide additional support for the hydrogel layer. It is preferable to have a support layer made of a polymeric film and a second support layer made from, for example, scrim adhesively secured to the support layer, both of which are interposed between the hydrogel layer and the substrate. As is apparent, the structure of the bandage resembles the conventional bandage presently used commercially. The polyurethane hydrogel material of the bandage comprises: (a) from about 0% to about 90% by weight polyhydric alcohol; (b) from about 6% to about 60% by weight isophoronediisocyanate terminated prepolymer; (c) from about 4% to about 40% by weight polyethylene oxide based diamine; (d) up to about 2% by weight sodium chloride; and (e) the balance water. Optionally, the bandage may further comprise a release liner disposed on the hydrogel layer to prevent contaminants from contacting the hydrogel layer prior to use.

In accordance with another aspect of the invention, the bandage comprises a substrate having a first side and a second side. The substrate further comprises a plurality of layers including a backing layer which forms the first side of the substrate, and an adhesive layer which forms the second side of the substrate. The bandage also comprises a hydrogel layer disposed over the second side of the substrate which is made from a polyurethane hydrogel material suitable for absorbing bodily fluids. The layers of the substrate are each formed of a transparent material while the hydrogel material is rendered transparent also such that visual inspection of a wound on which the bandage is mounted is possible without removing the bandage.

Accordingly, it is an object of the present invention to provide a bandage of the self-adhesive type which includes a material having the ability to absorb sufficient amounts of wound exudate and other body fluids and satisfactorily promote the healing of the wound yet maintain its structural integrity even upon removal of the bandage from the wound; and to provide a bandage which permits visual inspection of the wound without removing the bandage from the wound. Other objects and advantages of the invention will be apparent from the following detailed description, the accompanying drawings and the appended claims.

DETAILED DESCRIPTION OF THE PREFERRED EMBODIMENT

Figure 1:
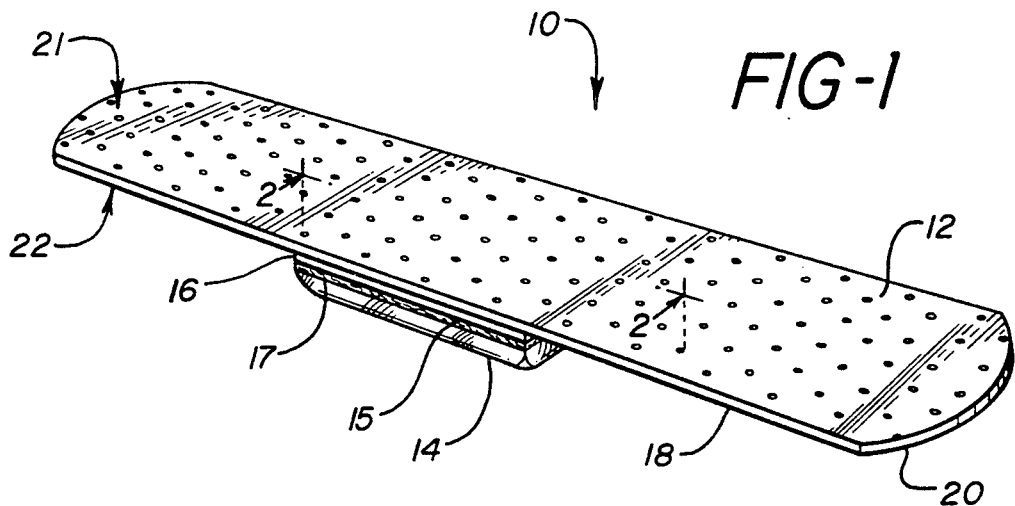
FIG. 1 is a perspective view of the bandage in accordance with the present invention.

FIG. 1 is a perspective view of a bandage 10 of the self-adhesive type in accordance with the invention. The bandage 10 comprises a substrate 12 substantially forming the outer portion thereof and having a first side 21 and a second side 22 which contacts the skin of a patient P (shown in FIG. 3). The bandage 10 further comprises a hydrogel layer 14 and optionally, a support layer 16, and/or a second support layer 17, which is secured to the support layer 16 with an adhesive layer 15. It should be understood, however, that the support layers 16 and 17 may be thermally as well as adhesively secured of the various layers within the bandage 10. Both support layers 16 and 17 provide additional support for the hydrogel layer 14 which is typically formed of a heavy and tacky material.

Figure 2:
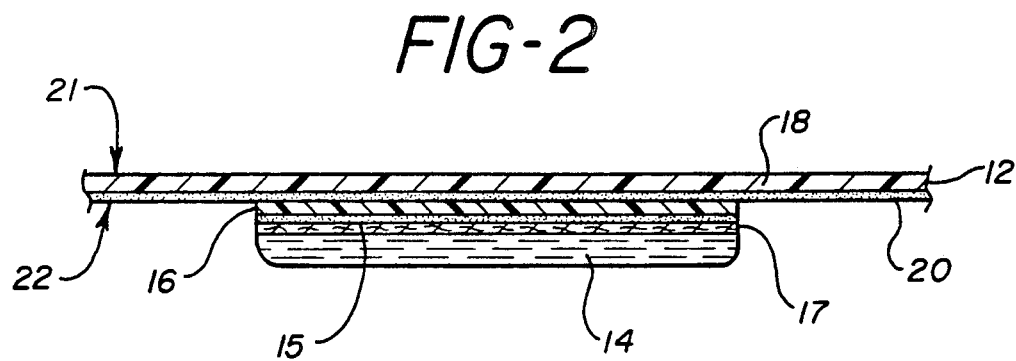
FIG. 2 is a cross-section view of the bandage taken along view line 2—2 in FIG. 1.

As best seen in FIG. 2, the substrate 12 comprises a backing layer 18 and a pressure sensitive adhesive layer 20 coated onto the second side 22 of the substrate 12 for contacting the skin of the patient P. The second side 22 is also referred to herein as a side f the backing layer 18 for contacting the skin of a patient. The hydrogen layer 14 is secured to the support layer 17 which is adhesively secured to the support layer 16 with the adhesive layer 15. Further, the support layer 16 is secured to the second side 22 which has the adhesive layer 20 coated thereon. The hydrogel layer 14 is preferably formed of a polyurethane hydrogel material suitable for absorbing bodily fluids including would exudate, perspiration, and the like. Polyurethane hydrogel provide substantial benefits over other materials in terms of bodily fluid absorption and ability to promote healing without adhering to wounds.

Figure 3:
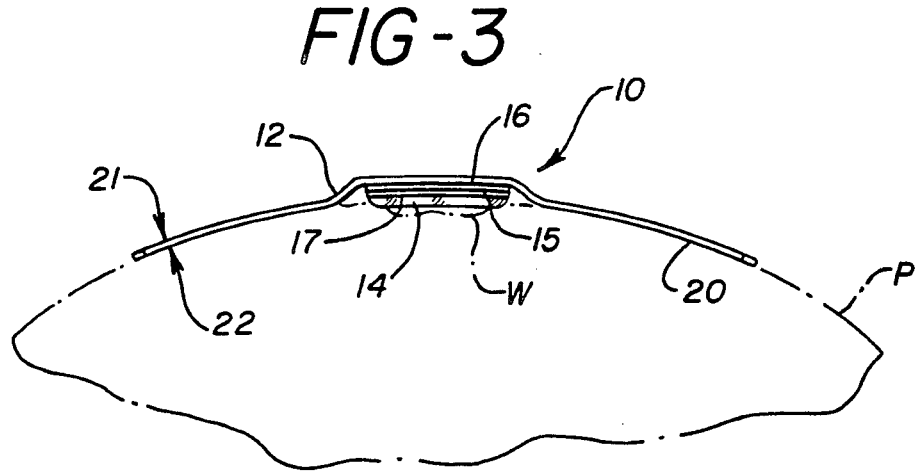
FIG. 3 is a schematic side view of the bandage being mounted on a wound found on a patient.

As can be seen in FIGS. 1-3, the second side 22 of the substrate 12 comprises a first portion being formed of the adhesive layer 20 and a second portion being formed of the hydrogel layer 14. The backing layer 18 is preferably formed from a polymeric material including but not limited to polyethylene terphtalate (commercially available from E.I. DuPont de Nemours & Co. under the trademark Mylar ®), polystyrene, polyethylene, polypropylene and polyvinylchloride. The adhesive layer 20 is peferably formed of a pressure sensitive adhesive material generally referred to in the art as "patient contact" adhesives which are well known. Typically, "patient contact" adhesives will be acrylic based, or elastomeric having a resin dispersed therein. The support layer 16 is preferably also formed from a polymeric material, such as those described above with reference to the backing layer 18. Preferably, the support layer 17 is made from a material such as woven and nonwoven fabrics, scrim and other similar materials. It should be understood that the support layers 16 and 17 are optional components according of the invention and are in clued only for the purpose of providing additional support for the hydrogel layer 14. Such additional support is required since the hydrogel layer 14 is preferably formed of a polyurethane hydrogel material which is hydrophilic, heavy and tack. It is preferable, however, that the support layers 16 and 17, as well as the adhesive layer 15, be coextensive with the hydrogel layer 14 as shown in FIG. 1. The adhesive layer 15 may be formed of any known adhesive which may adhesively secure the support layer 17 to the support layer 16. Those skilled in the art should appreciate that the aforementioned components of the bandage 10 may be formed of other materials beyond those described herein.

As stated above, the hydrogel layer 14 is preferably formed form a polyurethane hydrogel material which is discussed more fully below. It should be understood, however, that the invention contemplates having the hydrogel layer 14 formed of any hydrogel material. Polyurethane hydrogel are preferred in accordance with the present invention since this particular class of hydrophilic gels provides excellent attributes for the bandage 10. In particular, polyurethane hydrogel provide a biocompatible, non-irritating, fluid absorbing, bacterial protective, cushioning and skin-like textured material. Although it is preferable to use a polyurethane hydrogel, those skilled in the art should appreciate that any hydrogel material having the aforementioned characteristic may be used in accordance with the invention. As stated previously, polyurethane hydrogel are particularly preferred since they have been found to possess characteristics which are extremely suitable for minor wounds such as cuts, abrasions and the like. Furthermore, polyurethane hydrogel permit the transmission of air and vapor, thereby promoting the healing process.

The preferred polyurethane hydrogel material comprises: (a) from about 0% to about 90% by weight polyhydric alcohol; (b) from about 6% to about 60% by weight isophoronediisocyanate terminated prepolymer; (c) from about 4% to about 40% by weight polyethylene oxide based diamine; (d) up to about 2% by weight sodium chloride; and (e) the balance water. The polyhydric alcohol is preferably selected from the group consisting of polypropylene glycol, polyethylene glycol and glycerine. Most preferably, the polyurethane hydrogel material comprises: (a) from about 15% to 30% by weight polypropylene glycol; (b) from about 8% to 14% by weight isophoronediisocyanate terminated prepolymer; (c) from about 5% to 10% by weight polyethylene oxide based diamine; (d) up to 1% by weight sodium chloride; and (e) the balance water. Most preferably, the polyurethane hydrogel material comprises: (a) from about 16% to 17% by weight polypropylene glycol; (b) from about 10% to 12% by weight isophoronediisocyanate terminated prepolymer; (c)

from about 7% to 9% by weight polyethylene oxide based diamine; (d) about .5% to 1% by weight sodium chloride; and (e) the balance water.

The isophoronediisocyanate terminated polymer is preferably based on polyols containing more than about 40% polyethylene oxide and having an isocyanate content of about 3% by weight. The molecular weight is preferably in a range from 1500–8000 and most preferably, from about 4000 to 5000. The molecular weight of the polyethylene oxide based diamine is preferably in a range from about 200 to 6000 and most preferably, about 2000. Those skilled in the art will appreciate that all of the constituents with the preferred hydrogel material may be readily synthesized or purchased commercially.

The bandage 10 may also include a release liner disposed on the second side 22 to prevent contaminants from contacting the hydrogel layer 14 and/or adhesive layer 20 prior to use. Such release liners are well known in the art and may be disposed directly onto the second side 22 of the substrate 12 as the hydrogel layer 14 and the adhesive layer 20 possess sufficient adhesive qualities to adhere to the release liner. Optionally, the release liner may be coated with a silicone polymer or similar compound to facilitate removal of the release liner.

Referring now to FIG. 3, the patient P having a wound W, is shown to have the bandage 10 disposed on the skin such that the hydrogel layer 14 substantially covers the wound W. It is possible to have all of the components of the bandage 10 formed of transparent materials such that the wound W may be visually observed and inspected as it heals without removing the bandage 10. This feature of the bandage 10 eliminates, or at least minimizes the necessity of frequent removal of the bandage 10 from the wound W. Additionally, the various components of the bandage 10 may be formed from materials which permit the transmission of air and vapor so as to facilitate further the healing of the wound W. For example, the substrate 12 as well as the support layers 16 and 17 may be perforated or scored with holes or apertures to readily permit the passage of air and vapor. In this way, bacterial proliferation and the formation of incrustations and the like in the wound W is minimized.

The bandage 10 may be fabricated by applying each of the aforedescribed components in the preferred structural configuration by way of a multitude of procedures. For example, one method contemplates forming each of the components individually in the form of elongated laminates, and then, laminating the components together in the desired layered configuration. Thereafter, the aggregated lamination is cut or stamped into the desired shape for the bandage 10. Alternatively, the adhesive layer 20 can be applied as a viscous liquid onto the backing layer 18 and then allowed to cure, or it may be applied in its cured state, typically as a thick, viscous gel, directly onto the backing layer 18. The support layers 16 and 17, if used, can then be applied to the central portion of the adhesive layer 20 followed by disposing the hydrogel layer 14 coextensively thereon. The hydrogel layer 14 may be disposed by applying the preferred polyurethane hydrogel material onto the second side 22 or onto whichever of the support layers 16 and 17 is used while the hydrogel material is in its uncured liquid phase.

Thereafter, the polyurethane hydrogel material is allowed to cure before packaging the bandage 10. Those skilled in the art will appreciate that the polyurethane hydrogel material possesses the requisite adhesive qualities to adhere directly to the second side 22 of the substrate 12 or either of the support layers 16 and 17, if used. After the polyurethane hydrogel material has cured, any further packaging may be pursued, such as mounting the aforedescribed release liner. Regardless of the process used to form the components, the bandage 10 may be prepared individually, or it may be manufactured by preparing strips of adjacent bandages such that the strips may be severed to form the individual bandages 10. The bandage 10 may be packaged in the form of rolls in dispenser boxes which allow the bandage 10 to be withdrawn in the form of a continuous "tape" and removed from the release liner to which the bandage 10 is attached. It should be understood that other manufacturing schemes may be used to produce the bandage 10 in addition to those described herein without departing from the scope of the invention.

The bandage 10 may be formed in a variety of sizes and shapes, for example, rectangular, square, round, etc. Typically, the bandage 10 will be approximately 3.0 cm wide and 7.5 cm in length. The thickness of the backing layer 12 will be in a range from approximately 20 microns to 100 microns, while the adhesive layer 20 will have a thickness in a range from approximately 20 microns to 60 microns. The support layer 16, if used, will have a thickness in a range from approximately 10 microns to 30 microns. Finally, the hydrogel layer 14 will typically have a thickness in range from approximately 600 microns to 1500 microns.

The bandage 10 is applied to the wound W by initially removing any prepackaging, such as the release liner and/or other protective packaging materials, while avoiding exposure of the hydrogel layer 14 and the adhesive layer 20 to contaminants. The hydrogel layer 14 is contacted with the wound W and the first portion of the second side 22, which comprise the adhesive layer 14, is pressed against the skin surrounding the wound W, firmly securing the entire bandage 10 to the patient P. Once applied, the air and moisture transmissive components of the bandage 10 allow air and moisture to penetrate to and from the wound W which promotes the healing process. As discussed above, the bandage 10 may be made entirely of transparent materials to allow for periodic inspection of the wound W. Accordingly, after the wound W has healed sufficiently as determined visually, the patient P may remove the bandage 10 from the wound W.

Having described the invention in detail and by reference to preferred embodiments thereof, it will be apparent that modifications and variations are possible without departing from the scope of the invention which is defined in the appended claims. For example, bandages with shapes and sizes other than those described herein may be used in accordance with the present invention.

What is claimed is:

1. A bandage comprising:
   a backing layer having first and second sides wherein said first side is adapted to face a sin surface of a patient and said second side faces opposite said first side;
   a pressure sensitive adhesive layer coated onto said first side of said backing layer, said adhesive layer having first and second end portions which are capable of adhering to the skin surface of said patient;

a support layer having first and second sides wherein said first side of said support layer is adhered to said adhesive layer; and a hydrogel layer formed on said second side of said support layer such that said support layer provides rigidity for said hydrogel layer, said hydrogel layer being located intermediate said first and second end portions and substantially coextensive with said adhesive layer to the extent that said first and second end portions of said adhesive layer are exposed for adhering to the skin surface of said patient, said hydrogel layer comprising a polyurethane hydrogel material suitable for absorbing bodily fluids.

2. The bandage of claim 1 wherein said backing layer is perforated with apertures for enhancing the transmission of air and vapor.

3. The bandage of claim 1 further including a second support layer positioned between said support layer and said hydrogel layer formed of a material selected from the group consisting of fabrics and scrim.

4. The bandage of claim 1 wherein said polyurethane hydrogel material comprises:
(a) from about 0% to about 90% by weight polyhydric alcohol;
(b) from about 6% to about 60% by weight isophoronediisocyanate terminated prepolymer;
(c) from about 4% to about 40% by weight polyethylene oxide based diamine;
(d) up to about 2% by weight sodium chloride; and
(e) the balance water.

5. The bandage of claim 4 wherein said polyhydric alcohol is selected from the group consisting of polypropylene glycol, polyethylene glycol and glycerine.

6. A wound dressing product of claim 1 wherein said polyurethane hydrogel material comprises:
(a) from about 15% to 30% by weight polypropylene glycol;
(c) from about 5% to 10% by weight polyethylene oxide based diamine;
(d) up to 1% by weight sodium chloride; and
(e) the balance water.

7. The bandage of claim 1 further comprising a release liner disposed on said hydrogel layer to prevent contaminants from contacting said hydrogel layer prior to use.

8. The bandage of claim 1 wherein said backing layer is made from a polymeric material.

9. A bandage comprising:
a substrate having a first side and a second side wherein said second side is adapted to face a skin surface of a patient and said first side faces opposite said second side, said substrate comprising a plurality of layers including
a backing layer which forms said first side of said substrate; and
an adhesive layer which forms said second side of said substrate, said adhesive layer having first and second end portions for adhering to the skin surface;
a support layer having first and second sides wherein said first side of said support layer is adhered to said adhesive layer; and
a hydrogel layer formed on said second side of said support layer such that said support layer provides rigidity for said hydrogel layer, said hydrogel layer being located intermediate said first and second end portions and substantially coextensive with said adhesive layer of the extent that said first and second end portions of said adhesive layer are exposed for adhering to the skin surface of said patient, said hydrogel layer comprising a polyurethane hydrogel material suitable for absorbing bodily fluids.

10. The bandage of claim 9 wherein said support layer is substantially coextensive with said hydrogel layer.

11. The bandage f claim 9 wherein said polyurethane hydrogel material comprises:
(a) from about 0% to about 90% by weight polyhydric alcohol;
(b) from about 6% to about 60% by weight isophoronediisocyanate terminated prepolymer;
(c) from about 4% to about 40% by weight polyethylene oxide based diamine;
(d) up to about 2% by weight sodium chloride; and
(e) the balance water.

12. The bandage of claim 11 wherein said polyhydric alcohol is selected from the group consisting of polypropylene glycol, polyethylene glycol and glycerine.

13. A wound dressing product of claim 9 wherein said polyurethane hydrogel material comprises:
(a) from about 15% to 30% by weight polypropylene glycol;
(b) from about 8% to 14% by weight isophoronediisocyanate terminated prepolymer;
(c) from about 5% to 10% by weight polyethylene oxide based diamine;
(d) up to 1% by weight sodium chloride; and
(e) the balance water.

14. The bandage of claim 9 wherein said layers of said substrate are each formed of a transparent material and wherein said hydrogel material is transparent such that visual inspection of a wound to which said bandage is mounted is possible without removing said bandage.

15. A bandage comprising:
a substrate having a first side and a second side wherein said second side is adapted to face a skin surface of a patient and said first side faces opposite to said second side, said substrate comprising a plurality of layers including
a backing layer which forms said first side of said substrate; and
a pressure sensitive adhesive layer which forms said second side of said substrate, said adhesive layer having first and second end portions for adhering to the skin surface;
a first support layer having first and second sides wherein said first side of said support layer is coextensively secured to said second side of said substrate such that said first and second end portions of said adhesive layer are exposed for adhering to the skin surface of said patient;
a second support layer made from scrim which is coextensively secured to said second side of said first support layer; and
a hydrogel layer impregnated in said second support layer opposite said second side of said first support layer, said second support layer providing rigidity and support for said hydrogel layer, wherein said hydrogel layer is substantially coextensive with said adhesive layer to the extent that said first and second end portions of said adhesive layer are exposed for adhering to the skin surface of said patient, said hydrogel layer being made form a polyurethane hydrogel material suitable for absorbing bodily fluids wherein said polyurethane hydrogel material comprises (a) from about 0% to about 90% by weight polyhydric alcohol;
(b) from about 6% to about 60% by weight isophoronediisocyanate terminated prepolymer;
(c) from about 4% to about 40% by weight polyethylene oxide based diamine;
(d) up to about 2% by weight sodium chloride; and
(e) the balance water.

16. The bandage f claim 15 further comprising a release liner disposed on said second side of said substrate to prevent contaminants from contacting said hydrogel layer and said adhesive layer prior to use.

17. The bandage of claim 15 wherein said polyhydric alcohol is selected from the group consisting of polypropylene glycol, polyethylene glycol and glycerine.

18. The bandage of claim 15 wherein said substrate is perforated with apertures for enhancing the transmission of air and vapor.

19. The bandage of claim 15 wherein said layers of said substrate are each formed of a transparent material and wherein said hydrogel material is transparent such that visual inspection of a wound to which said bandage is mounted is possible without removing said bandage.

* * * * *

UNITED STATES PATENT AND TRADEMARK OFFICE
CERTIFICATE OF CORRECTION

PATENT NO.  : 5,160,328

DATED       : November 3, 1992

INVENTOR(S) : Cartmell et al

It is certified that error appears in the above-identified patent and that said Letters Patent is hereby corrected as shown below:

Col. 6, line 62,    "sin surface" should read --skin surface--.

Col. 7, between lines 37 and 38, please insert
          --(b)  from about 8% to 14% by weight
                 isophoronediisocyanate terminated
                 prepolymer;--.

Col. 9, line 9,    "bandage f" should read --bandage of--.

Signed and Sealed this

Twenty-sixth Day of October, 1993

Attest:

BRUCE LEHMAN

Attesting Officer

Commissioner of Patents and Trademarks